US010390910B2

(12) United States Patent
Jo et al.

(10) Patent No.: US 10,390,910 B2
(45) Date of Patent: Aug. 27, 2019

(54) INTEGRATED DENTAL IMPLANT COMPONENT AND TOOL FOR PLACEMENT OF A DENTAL IMPLANT COMPONENT

(71) Applicant: DENTSPLY INTERNATIONAL INC., York, PA (US)

(72) Inventors: Jeremy E. Jo, Somerville, MA (US); Jeffrey Miles Ragazzini, Medford, MA (US); James G. Hannoosh, West Barnstable, MA (US); Terry G. Lorber, II, Swampscott, MA (US)

(73) Assignee: DENTSPLY SIRONA INC., York, PA (US)

(*) Notice: Subject to any disclaimer, the term of this patent is extended or adjusted under 35 U.S.C. 154(b) by 615 days.

(21) Appl. No.: 14/811,172

(22) Filed: Jul. 28, 2015

(65) Prior Publication Data
US 2016/0000534 A1 Jan. 7, 2016

Related U.S. Application Data

(63) Continuation of application No. 14/228,373, filed on Mar. 28, 2014.

(60) Provisional application No. 61/805,962, filed on Mar. 28, 2013.

(51) Int. Cl.
*A61C 8/00* (2006.01)
*A61C 9/00* (2006.01)

(52) U.S. Cl.
CPC .......... *A61C 8/0089* (2013.01); *A61C 8/0001* (2013.01); *A61C 8/0018* (2013.01); *A61C 8/0022* (2013.01); *A61C 8/0087* (2013.01); *A61C 9/004* (2013.01)

(58) Field of Classification Search
CPC .......................... A61C 8/0087; A61C 8/0089
See application file for complete search history.

(56) References Cited

U.S. PATENT DOCUMENTS

| 5,350,297 A | 9/1994 | Cohen | |
| 5,690,489 A | 11/1997 | Carchidi | |
| 5,944,525 A * | 8/1999 | Ura | A61C 8/0089 433/141 |
| 7,300,284 B2 * | 11/2007 | Linder | A61C 8/0022 433/172 |
| 8,226,410 B2 * | 7/2012 | Kim | A61C 8/0089 433/174 |
| 8,275,184 B2 | 9/2012 | Schneider et al. | |
| 8,282,395 B2 * | 10/2012 | Schaffran | A61C 8/0089 433/173 |
| 8,602,777 B2 * | 12/2013 | Way | A61C 7/02 433/141 |
| 8,632,337 B2 | 1/2014 | De Clerck | |

(Continued)

FOREIGN PATENT DOCUMENTS

| CA | 2672363 | * | 6/2008 |
| CA | 2672363 A1 | | 6/2008 |

(Continued)

*Primary Examiner* — Edward Moran
(74) *Attorney, Agent, or Firm* — McNees Wallace & Nurick LLC

(57) ABSTRACT

An integrated dental component, carrier and affixation tool provides a clinician with a large object to hold the dental component, and allows for single-handed orientation, placement and fastening with the integration of an affixation tool.

10 Claims, 4 Drawing Sheets

(56) References Cited

U.S. PATENT DOCUMENTS

| | | |
|---|---|---|
| 2005/0266379 A1 | 12/2005 | Kumar et al. |
| 2006/0246399 A1* | 11/2006 | Ehrl ................. A61C 8/0012 433/201.1 |
| 2007/0037121 A1* | 2/2007 | Carter ............... A61C 8/0089 433/173 |
| 2008/0014556 A1* | 1/2008 | Neumeyer ......... A61C 8/0022 433/174 |
| 2008/0176188 A1 | 7/2008 | Holzner et al. |
| 2010/0296710 A1 | 11/2010 | Schneider et al. |
| 2012/0135371 A1 | 5/2012 | Jahn |
| 2012/0141951 A1 | 6/2012 | Bellanca et al. |
| 2012/0164599 A1 | 6/2012 | Holmstrom et al. |
| 2014/0011155 A1 | 1/2014 | Thomsen |

FOREIGN PATENT DOCUMENTS

| | | |
|---|---|---|
| EP | 1920730 A2 | 5/2008 |
| EP | 2130514 A1 | 12/2009 |
| EP | 2462893 A1 | 6/2012 |
| WO | 02/080804 A1 | 10/2002 |
| WO | 2012/126475 A1 | 9/2012 |
| WO | 2012/156064 A1 | 11/2012 |

\* cited by examiner

INTEGRATED DENTAL IMPLANT COMPONENT AND TOOL FOR PLACEMENT OF A DENTAL IMPLANT COMPONENT

CROSS-REFERENCE TO RELATED APPLICATION

This application is a continuation of U.S. patent application Ser. No. 14/228,373, filed Mar. 28, 2014, which claims benefit of U.S. patent application No. 61/805,962, filed Mar. 28, 2013.

TECHNICAL FIELD

The present invention is directed toward the placement of components into the oral cavity. More particularly, the invention relates to an integrated component and carrier.

BACKGROUND OF THE INVENTION

During dental procedures especially those involving dental implants and the like, the clinician must often grab, carry, orient, and then place the dental component into the correct position in the patient's mouth. While holding onto the dental component to prevent the soft tissue from ejecting the component, the clinician will often use his or her other hand to rotate screw driver to fix the part in place. Because of the small size of the dental components, often only 15 mm in length at most, the parts are difficult to handle and grasp, especially in the vicinity of neighboring teeth. This is farther exacerbated by a clinician's reduced dexterity when wearing gloves.

A need exists for a tool and component that will facilitate the grasping, manipulation, placement and orientation of such components. By "component" as used herein it is intended to mean any device or construct useful in dental procedures, such as for example, implants, implant abutments, dental appliances, and the like. The invention is exemplified herein with respect to a scan flag as may be used during dental implant treatment procedures.

SUMMARY OF THE INVENTION

An integrated dental component and tool driver according to the present invention comprises two features that are integrated into one device. The lower portion of the driver features an asymmetrical, conical taper. The conical taper provide a friction fit engagement between an outer surface of the lower driver component and an inner surface of the dental component such as a scan flag while maintaining the ability to turn, and rotate the component. The upper portion of the driver is a screwdriver or other device that allows the clinician to tighten the screw inside the dental component or otherwise manipulate its affixation mechanism.

PREFERRED EMBODIMENTS FOR CARRYING OUT THE INVENTION

Figures 6, 7:
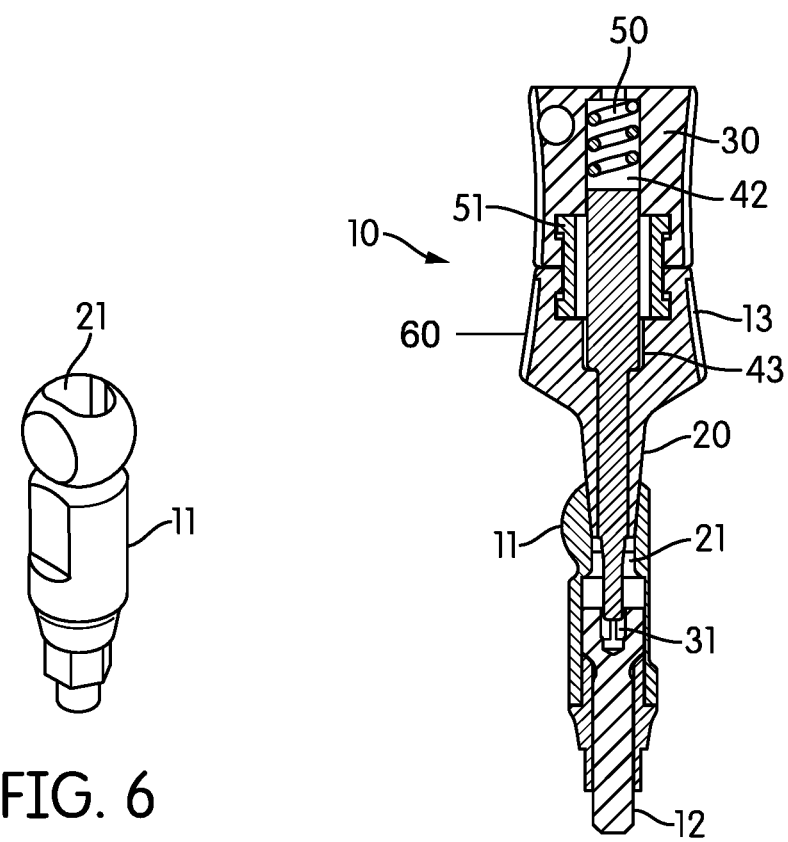
FIG. 6 is a perspective view of one portion of the integrated tool of FIG. 1
FIG. 7 is a sectional, side devotional view of the integrated tool of FIG. 5.

The drawing figures show an integrated device 10 according to the present invention, that assists a clinician in the handling, placement, orientation, and fixation of a dental component, such as an otherwise conventional, screw-retained dental scan flag 11 to the oral cavity, such as to a dental implant 12 (FIG. 7). The dental component to be placed may be for example, a dental scan flag 11 as shown on the drawings, which digitally registers the location of an implant inside a patient's mouth. However, the driver assembly 10 can also be configured for use with a variety of dental components, including for example, impression transfers and pick-ups, abutments, healing caps, healing abutments and the like (not shown).

The preferred driver has two features that are integrated into one device. The lower portion 13 of the driver 10 has a notched gripping segment 60 extending to an asymmetrical, conical taper 20. The dental component 11 has an aperture 21 which is preferably complementary in shape to taper 20. Taper 20 is receivable within aperture 21 to provide a friction fit engagement between as shown in FIG. 7. An upper portion 30 of the driver is a screwdriver 31 or other tool useful with component 11 as will be described hereinbelow.

Figure 1:
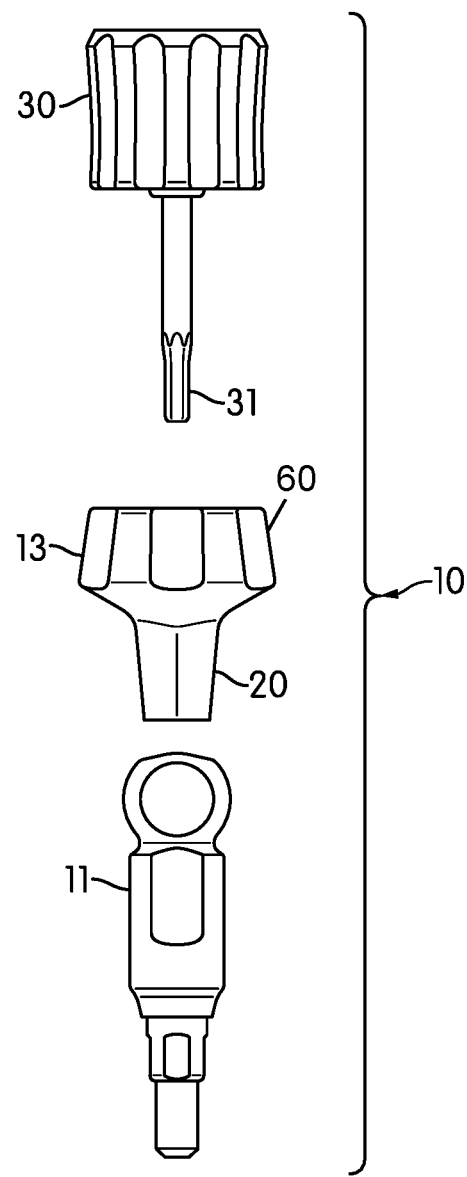
FIG. 1 is an exploded view of an integrated dental component and tool according to the concepts of the present invention.
Figure 2:
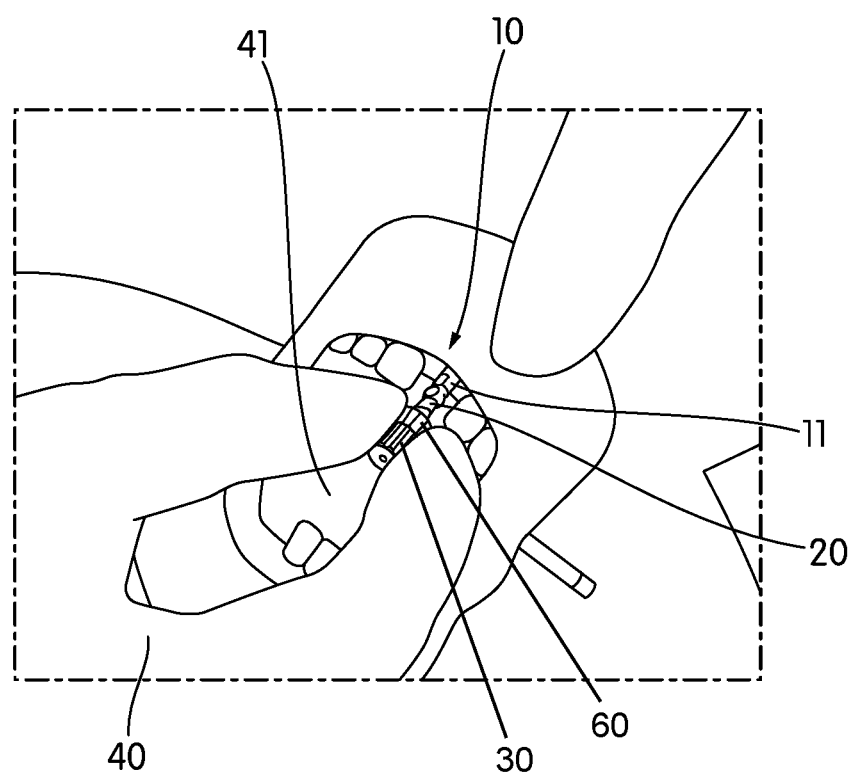
FIG. 2 is a perspective view of the non-exploded integrated toot of FIG. 1, shown being manipulated in the oral cavity.
Figure 5:
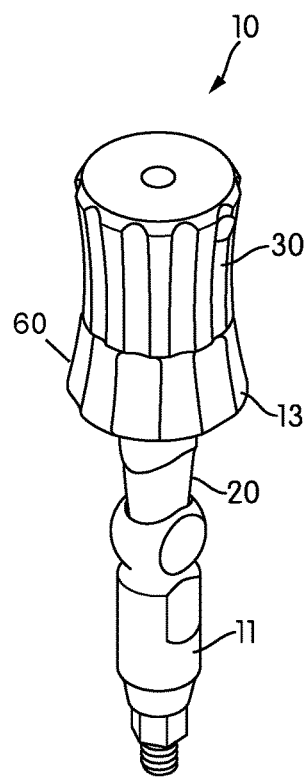
FIG. 5 is a non-exploded view of the integrated tool of FIG. 1.

As shown in FIGS. 2 and 5, the device 10 is configurable such that the component 11 receives taper 20. Thus as is shown in FIG. 2, the clinician 40 may grasp, for example, at least one of the upper portion 30 and the gripping segment 60 of the lower portion 13 of the device 10, position it the device within the oral cavity 41 of the patient, manipulate the orientation of the component as necessary and otherwise place and affix the component 11 as needed.

The proposed carrier-driver concept provides a clinician with a larger object to hold the dental component 10, and also allows for single-handed orientation, placement and fastening with the integration of a tool such as screwdriver 31. The clinician does not need to hold the component in place with one hand, while using the other hand to tighten a screw driver as was required with the prior art. Once the component 11 (again, exemplified as a scan flag on the drawings) is attached to the driver assembly lower portion 13 and upper portion 30 (preferably accomplished, outside the mouth), the clinician only needs to handle one integrated driver component 10 instead of handling both the scan flag 11 and a driver separately 31. Once set in place, the driver assembly (13, 30) can easily be removed without the use of tools due to the friction fit between the dental component 11 and taper 20 as was described. Using the driver/carrier (13, 30) not only affords the clinician with single handed operation, but it also allows for more free space in the patient's mouth and provides better sight when locating and placing the dental components.

Figure 3:
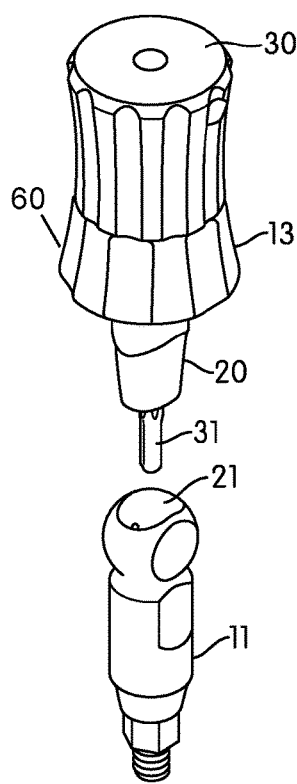
FIG. 3 is a partially exploded, perspective view of the integrated tool of FIG. 1.
Figure 4:
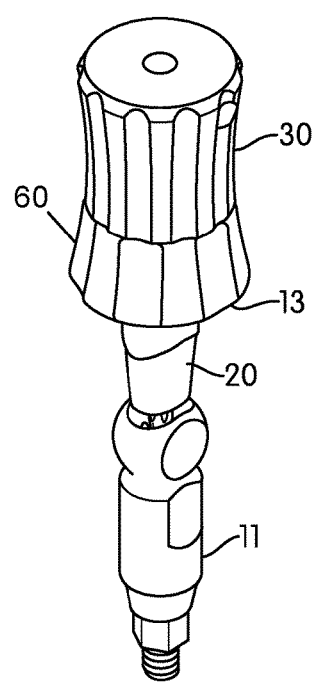
FIG. 4 is a partially exploded, perspective view of the integrated tool of FIG. 1.

FIGS. 3, 4 and 5 are a sequence showing an upper and lower portion 30, 13 assembled and being physically connected by the aforementioned friction fit. FIG. 3 shows the upper/lower 30/13 assembly separate from the scan flag 11. FIG. 4 depicts taper 20 partially inserted into complementary aperture 21, while FIG. 5 shows the taper 20 fully received within and frictionally secured within aperture 21, thereby forming the integrated tool 10. It will be appreciated that in the assembled version shown in FIG. 5, a clinician 40 may easily grasp, manipulate and place scan flag 11 within the oral cavity 41. While a friction fit is preferred, it will be appreciated that any means of securing lower portion 13 to scan flag 11 (or whatever component is employed) is within the scope of the invention. Further, it is also within the scope of the invention to not employ upper portion 30 at all or even to make upper portion 30 and lower portion 13 one, monolithic piece, all of which are within the scope of the invention.

In one embodiment of the invention, screwdriver 31 is retained within a bore 42 in upper portion 30 and may also project through a second bore 43 in lower portion 13. A bias means such as coil 50 may be placed within bore 42 to bias screwdriver 31 in a desired direction. There is also preferably a means to affix upper portion 30 to lower portion 13, such as clip 51 (FIG. 7).

The invention claimed is:

1. An integrated dental component and tool comprising:
   a dental component having a first longitudinal axis; and
   a tool comprising a lower portion having a second longitudinal axis, the lower portion comprising a gripping segment extending to an end portion having a continuous non-circular conical taper, the continuous non-circular conical taper extending about an entire periphery of the end portion relative to the second longitudinal axis, the end portion defining the continuous non-circular conical taper, the continuous non-circular conical taper providing a friction fit engagement between an external surface of the lower portion and an internal surface of the dental component during mutual alignment of the first longitudinal axis and the second longitudinal axis, such that rotating the tool effects rotation of the dental component, the gripping segment being selectably graspable by a clinician subsequent to the mutual alignment of the first longitudinal axis and the second longitudinal axis, an upper portion being removably received by a first bore in the lower portion, the tool further comprising:
      a bias member positioned within a second bore in the upper portion and biasing the tool driver in a predetermined direction, the bias member being a coil spring; and
   a tool driver retained in the upper portion, the tool driver extending through the lower portion, wherein the tool driver is a screwdriver.

2. An integrated dental component and tool as in claim 1, wherein the dental component is a scan flag.

3. An integrated dental component and tool as in claim 1, wherein the dental component has an aperture that receives at least a part of the lower portion in a removable manner.

4. An integrated dental component and tool as in claim 1, further comprising a clip affixing the upper portion to the lower portion.

5. An integrated dental component and tool as in claim 1, wherein the continuous non-circular conical taper is ovular.

6. A method of placing a dental component comprising the steps of:
   placing an integrated dental component and tool in a predetermined location, the integrated dental component and tool comprising the dental component having a first longitudinal axis and a tool comprising a lower portion having a second longitudinal axis and a gripping segment extending to an end portion having a continuous non-circular conical taper, the continuous non-circular conical taper extending about an entire periphery of the end portion relative to the second longitudinal axis, the end portion defining the continuous non-circular conical taper, the continuous non-circular conical taper removably receivable by the dental component, the continuous non-circular conical taper providing a friction fit engagement between an external surface of the lower portion and an internal surface of the dental component during mutual alignment of the first longitudinal axis and the second longitudinal axis, such that rotating the tool effects rotation of the dental component, the gripping segment being selectably graspable by a clinician subsequent to the mutual alignment of the first longitudinal axis and the second longitudinal axis, and an upper portion retaining a tool driver therein, the upper portion being removably received by a first bore in the lower portion with the tool driver extending through the lower portion, the tool further comprising:
      a bias member positioned within a second bore in the upper portion and biasing the tool driver in a predetermined direction, the bias member being a coil spring, wherein the tool driver is a screwdriver; and
   removing the tool from the dental component.

7. A method as in claim 6, further comprising rotating the upper portion thereby rotating the tool driver to rotate a screw to fasten the dental component in the predetermined location.

8. A method as in claim 6, further comprising physically manipulating the positioning of the dental component with the tool.

9. A method as in claim 8, wherein the placing, the physically manipulating, and the removing are performed using a single hand.

10. A method as in claim 6, wherein the removing is accomplished by hand without tools.

* * * * *